United States Patent [19]
Chandrasegaran

[11] Patent Number: 5,487,994
[45] Date of Patent: Jan. 30, 1996

[54] INSERTION AND DELETION MUTANTS OF FOKI RESTRICTION ENDONUCLEASE

[75] Inventor: Srinivasan Chandrasegaran, Baltimore, Md.

[73] Assignee: The Johns Hopkins University, Baltimore, Md.

[21] Appl. No.: 346,293

[22] Filed: Nov. 23, 1994

Related U.S. Application Data

[63] Continuation-in-part of Ser. No. 126,564, Sep. 27, 1993, which is a continuation-in-part of Ser. No. 17,493, Feb. 12, 1993, abandoned, which is a continuation-in-part of Ser. No. 862,831, Apr. 3, 1992, Pat. No. 5,356,802.

[51] Int. Cl.$^6$ ................................................. C12N 9/22
[52] U.S. Cl. ................................................. 435/199; 435/193
[58] Field of Search ................................... 435/199, 193

[56] References Cited

PUBLICATIONS

Bocklage, H., et al. (1991) Nucl. Acids Res. 19(5), 1007–1013.
Li, L., et al., (1992) Proc. Natl. Acad. Sci, USA 89, 4275–4279.
Kita K. et al., (1992) Nucl. Acids Res. 20(16), 4167–4172.
Li, L. et al. (1993) Gene 133, 79–84.
Waugh, P. S. et al. (1994) J. Biol. Chem. 269(16), 12,298–12,303.
Waugh, D. S., et al. (1993) Proc. Natl. Acad. Sci. USA 90, 9596–9600.
Li, L. et al., (1993) Proc. Natl. Acad. Sci., USA 90, 2764–2768.
Kim, Y. G., et al. (1994) Proc. Natl. Acad. Sci., USA 91, 883–887.

*Primary Examiner*—Charles L. Patterson, Jr.
*Attorney, Agent, or Firm*—Cushman Darby & Cushman

[57] ABSTRACT

The present invention reveals the construction of several insertion (4, 8, 12, 18, 19 or 23 amino acid residues) and deletion (4 or 7 amino acid residues) mutants of the linker region of *Fok*I endonuclease in *Flavobacterium okeanokoites*. The mutant enzymes were purified, and their cleavage properties were characterized. The mutants have the same DNA sequence-specificity as the wild-type enzyme. However, compared with the wild-type enzyme, the insertion mutants cleave predominantly one nucleotide further away from the recognition site on both strands of the DNA substrate. The four codon deletion mutant shows relaxed specificity at the cut site while the seven codon deletion appears to inactivate the enzyme. The DNA-binding and cleavage domains of *Fok*I appear to be linked by a relatively malleable linker. No simple linear relationship exists between the linker length and the distance of the cut site from the recognition site. Furthermore, the four codon insertion mutants cleave DNA substrates containing hemi-methylated *Fok*I sites; they do not cleave fully-methylated substrates.

10 Claims, 9 Drawing Sheets

XbaI
5'—GGCTCTAGACGGCGGTGGAGGATCAGGGGAGGAGGTAGC—3'
3'—CCCCTCCTCCATCGCCGCCTCCGCCCTAGTGTTGATCAGG—5'
                                        SpeI

FIG. 1

5'-CTAGAGTCAGATAGCGAAGACTTCGGGGATGGGCTTAATGGCCTTAGTTCACAA    -3'
3'-      TCAGTCTATCGCTTCTGAAGCCCCTACCCGAATTACCGGAATCAAGTGTTTCGA-5'

FIG. 3

5'—*pCTAGAGTCAGAATTCGAAGACTTGCCGGATGATCTGCAGGCCAGCTGTGGCGTCTAAATTGA —3'
3'—    TCAGTCTTAAGCTTCTGAACGGCCTACTAGACGTCCGGTCGACACCGCAGATTAACTTCGA*p—5'

FIG. 8

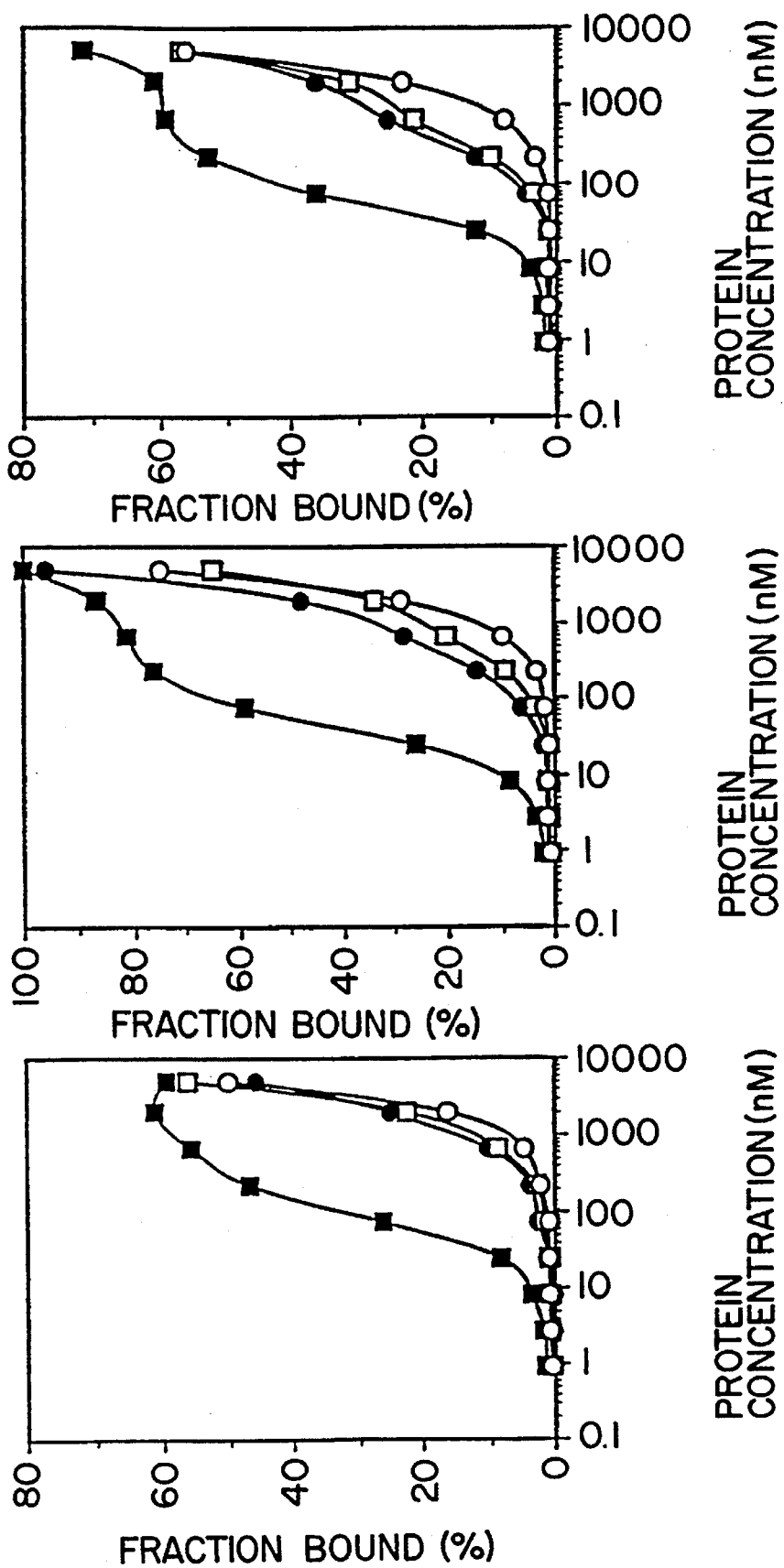

INSERTION AND DELETION MUTANTS OF FOKI RESTRICTION ENDONUCLEASE

The subject application is a continuation-in-part of application Ser. No. 08/126,564, filed Sept. 27, 1993, which has been allowed and is, in turn, a continuation-in-part of application Ser. No. 08/017,493, filed on Feb. 12, 1993, which has been abandoned and is, in turn, a continuation-in-part of application Ser. No. 07/862,831, which was filed on Apr. 3, 1992 and which issued as U.S. Pat. No. 5,356,802. All three parent continuation-in-part applications are hereby incorporated in their entirety by reference and relied upon.

This patent application was supported in part by grant GM 42140 from the National Institutes of Health. The Government has certain rights in the invention.

BACKGROUND OF THE INVENTION

1. Field of the Invention

The present invention relates to the construction of six insertion (4, 8, 12, 18, 19 or 23 amino acid residues) and two deletion (4 or 7 amino acid residues) mutants of the linker region of FokI endonuclease from Flavobacterium okeanokoites. The mutant enzymes were purified, and their cleavage properties have been characterized.

2. Description of the Related Art

The FokI restriction endonuclease from Flavobacterium okeanokoites belongs to the Type IIS class of endonucleases. FokI recognizes the asymmetric sequence 5'-GGATG-3' and cleaves double-stranded DNA at staggered sites 9 and 13 nucleotides away from the recognition site (1, 2). The cloning and sequencing of the FokI restriction-modification system have been reported (3-4). Several research groups have purified FokI endonuclease and characterized its properties (5-9). Previous reports by the present inventor on proteolytic fragments of FokI endonuclease using trypsin have revealed a N-terminal DNA-binding domain and a C-terminal catalytic domain with non-specific DNA cleavage activity (10,11). These reports have suggested that the two domains are connected by a linker region which is susceptible to cleavage by trypsin. The present inventor has also shown that insertion of four (or seven codons) between the recognition and cleavage domains of FokI can alter the cleavage distance of FokI within its substrate (12).

Recently, Waugh and Sauer have shown that single amino acid substitutions uncouple the DNA-binding and strand scission activities of FokI endonuclease (13). Furthermore, they have obtained a novel class of FokI restriction mutants that cleave hemi-methylated DNA substrates (14). The modular structure of FokI suggested that it may be feasible to construct hybrid endonucleases with novel sequence-specificity by linking other DNA-binding proteins to the cleavage domain of FokI endonuclease. Recently, the present inventor reported the construction of the first "chimeric" restriction endonuclease by linking the Ubx homeo domain to the cleavage domain of FokI (15).

To further probe the linker region, the present inventor has constructed several insertion and deletion mutants of FokI endonuclease. A detailed description of the process for making and using and the properties of these mutants follows.

SUMMARY OF THE INVENTION

The present invention discloses the construction of seven insertion (4, 4, 8, 12, 18, 19 or 23 amino acid residues) and two deletion (4 or 7 amino acid residues) mutants of the linker region of FokI endonuclease from Flavobacterium okeanokoites. The FokI endonuclease has an N-terminal DNA recognition domain, a C-terminal DNA cleavage domain and a linker region between these domains.

The insertion mutant FokI endonucleases of the present invention are characterized in that the distance recognized between the recognition site and the cleavage site of the DNA substrate is shifted one base pair away from the recognition site as compared to the distance between the recognition site and the cleavage site of the DNA substrate when wild-type enzyme is used.

The insertion mutants of the present invention are also characterized by having specific amino acid residues inserted between the recognition domain and the cleavage domain of the endonuclease.

The deletion mutants of the present invention are characterized by having specific amino acid residues deleted between the recognition domain and the cleavage domain of the endonuclease.

BRIEF DESCRIPTION OF THE DRAWINGS

FIG. 1 shows a duplex formed between oligonucleotide 5'-GGCTCTAGACGGCGGTGGAGGATCAGGGG GAG-GAGGGTAGC-3' (SEQ ID NO:1) and 5'-GGACTAGTTGTG ATCCGCCTCCGCCGCTACCTCCTCCCCC-3' (SEQ ID NO:2). The XbaI and SpeI restriction sites are indicated in bold-faced type.

FIG. 3 shows a duplex formed between oligonucleotide 5'-CTAGAGTCAGATAGCGAAGACTTCGGGGATG GGCTTAATGGCCTTAGTTCACAA-3' (SEQ ID NO:10) and 5'-AGCTTTGTGAACTAAGGCCATTAAGC-CCATCCCCGAAGTCTTCGCTATCT GACT-3' (SEQ ID NO:11). The FokI recognition site is indicated by the bold-faced type.

FIG. 7A, unmethylated substrate; FIG. 7B, hemi-methylated (5'-GGATG--3) substrate; FIG. 7C, hemi-methylated (5'-CATCC--3) substrate; and FIG. 7D, fully-methylated substrate. Lane 1, uncleaved substrates; lane 2, PuvII enzyme; lane 3, wild-type FokI; lane 4, TAEL (SEQ ID NO:4) insertion mutant; and lane 5, KSEL (SEQ ID NO:3) insertion mutant. The sequence of the substrate is shown in FIG. 8. The methylation sites are indicated by –CH$_3$. PuvII cleavage produces oligonucleotides 22-mer and 44-mer as products.

FIG. 8 shows a duplex formed between oligonucleotide 5'-CTAGAGTCAGAATTCGAAGACTTGCCGGATG ATCTGCAGGCCAGCTGTGGCGTCTAAATTGA-3' (SEQ ID NO:12) and 5'-AGCTTCAATTTAGACGCCA-CAGCTGGCCTGCAGATCATOCGGC AAGTCTTC-GAATTCTGACT-3' (SEQ ID NO:13). The FokI recognition site is indicated by the bold-faced type and the methylation sites are indicated by •, where Å represents $N_6$-methylated adenine residues.

FIGS. 9A, 9B and 9C graphically depict the affinity of wild-type FokI and four-codon, TAEL (SEQ ID NO:4) and KSEL (SEQ ID NO:3), insertion mutants for unmethylated, hemi-methylated and fully methylated DNA substrates determined using filter-binding assays in presence of non-specific DNA, poly (dI-dC). FIGS. 9A, 9B and 9C correspond to wild-type FokI, TAEL (SEQ ID NO:4) and KSEL (SEQ ID NO:3) insertion mutants respectively. ■, unmethylated substrate; ◐ hemi-methylated substrate where 5'-GGATG--3' is methylated; ■, hemi-methylated substrate where the complementary strand 5'-CATCC--3' is methylated and O, corresponds to the fully methylated substrate.

DETAILED DESCRIPTION OF THE INVENTION

Figure 2:
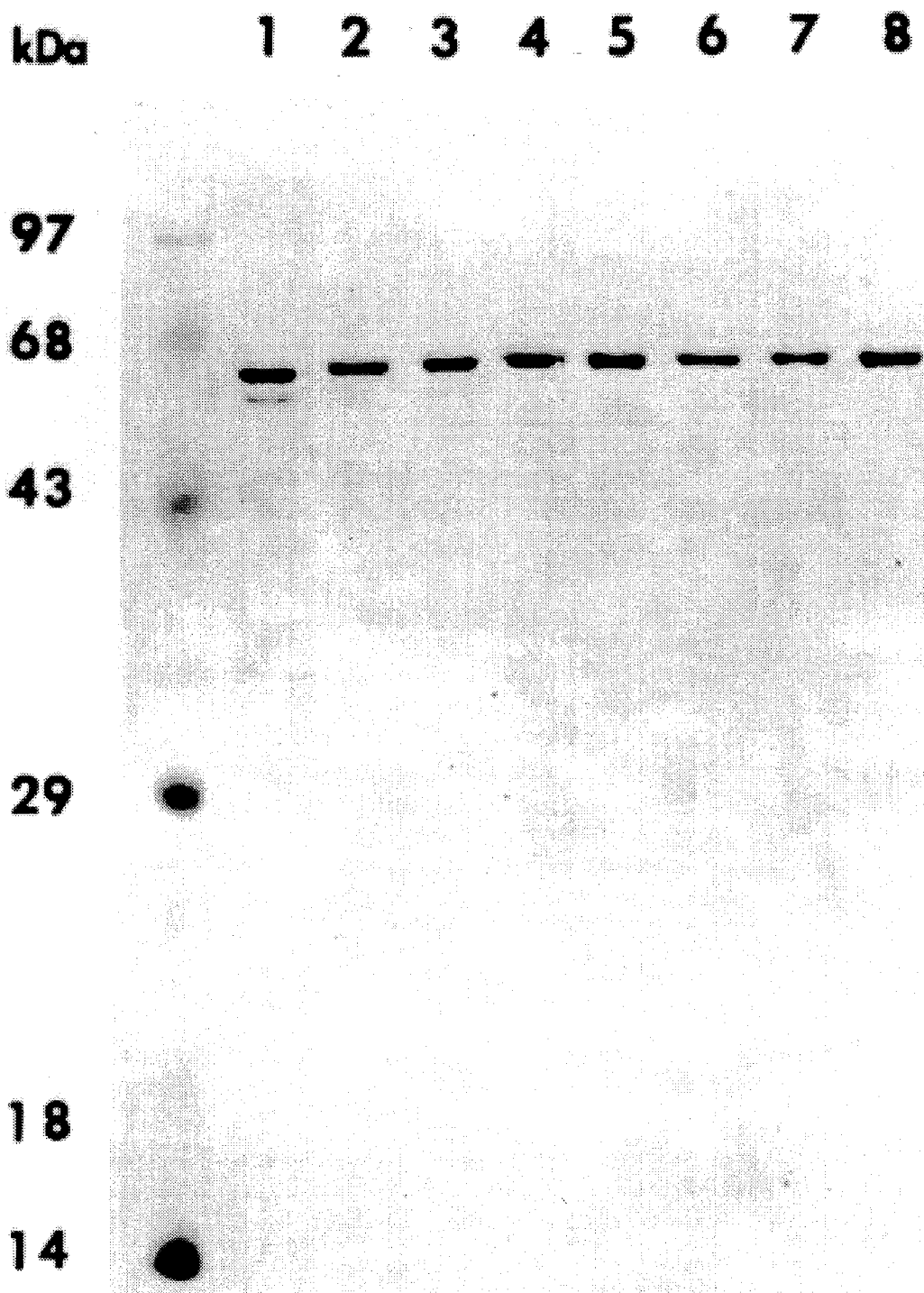
FIG. 2 shows the SDS/PAGE profiles of purified deletion and insertion mutants of FokI endonuclease. Lane 1, KSEL (SEQ ID NO:3) deletion; lane 2, wild-type FokI; lane 3, TAEL (SEQ ID NO:4) insertion; lane 4, TAELTAEL (SEQ ID NO:5) insertion; lane 5, TAELTAELTAEL (SEQ ID NO:6) insertion; lane 6, 19 amino acid residue insertion, TAELTAELKSELKSELEEK (SEQ ID NO:7); lane 7, 23 amino acid residue insertion, TAELTAELTAEL KSELK-SELEEK (SEQ ID NO:8); and lane 8, glycine linker insertion, RGGGGSGGGGSGGGGSQL (SEQ ID NO:9).

The present invention details the construction of seven insertion mutants (4, 4, 8, 12, 18, 19 or 23 amino acid residues) and two deletion mutants (4 or 7 amino acid residues) of the linker region of FokI endonuclease from *Flavobacterium okeanokoites*.

The insertion mutants have an amino acid residue insertion between the recognition domain and the cleavage domain where the insertion is selected from the group consisting of SEQ ID NO:3, 4, 5, 6, 7, 8 and 9.

The deletion mutants have an amino acid residue deletion between the recognition domain and the cleavage domain where the deletion consists of KSEL (SEQ ID NO:3) or KSELEEK (SEQ IN NO:14).

The insertion and deletion mutant endonucleases of the present invention were prepared and characterized as follows:

EXPERIMENTAL PROCEDURES

*E. coli* RR1 strain was the host in all experiments. RR1[pACYCfokIM] which carries a single copy of the FokI methyltransferase gene (fokIM) was used for the construction and expression of the insertion and deletion mutants of FokI endonuclease.

The mutant genes were cloned into pRRS under the control of lacUV5 promoter. The detailed structure of pRRSfokIR and pACYCfokIM have been published previously (10). The pTZ19R plasmid DNA was used as the substrate to assay the activity of the mutant enzymes.

Construction of insertion and deletion mutants of FokI endonuclease

The PCR technique was used to insert or delete amino acid residues within the proposed linker region of FokI endonuclease as previously reported (12). The PCR generated DNA containing the insertions or deletions were digested with SpeI/SmaI and gel-purified. The plasmid pRRSfokIR that contains a single SpeI site within the fokIR gene was cleaved with SpeI/SmaI, and the large 3.9-kb fragment was gel-purified and ligated to the PCR product.

After selection on LB plates containing tetracylin (20 μg/ml) and ampicillin (60 μg/ml), the plasmid DNA from the surviving clones were screened for larger SpeI/HindIII inserts as compared to the wild-type fragment by agarose (1.5%) gel electrophoresis. The cultures of the positive clones were induced with isopropyl-β-D-thiogalactopyranoside (IPTG). After sonication, the mutant enzymes were partially purified using a phosphocellulose column and then were assayed for restriction endonuclease activity.

In addition, the recombinant plasmids from the active clones were isolated and the presence of the insertions or deletions were confirmed by Sanger's dideoxy sequencing method (16). The construction of the RGGGGSGGGGSGGGGSQL (SEQ ID NO:9) insertion mutant containing the glycine linker (Gly$_4$Ser)$_3$ (SEQ ID NO:15) was done by synthesizing the appropriate complementary oligonucleotides. The oligonucleotides were annealed to yield the duplex shown in FIG. 1. The duplex is flanked by XbaI and SpeI restriction sites. The annealed duplex was filled-in by using dNTPs and Klenow fragment to generate the XbaI and SpeI sites. The duplex was then digested with SpeI/XbaI, purified using G-25 spun column and then ligated into SpeI-cleaved pRRSfokIR plasmid.

The recombinants were screened for appropriate inserts using SpeI/ScaI/HindIII enzyme digestion. The presence of the insert in the right orientation within the gene was confirmed by using Sanger's dideoxy sequencing method (16).

Overproduction and purification of the mutant enzymes

The procedures for cell growth and purification of the mutant enzymes are similar to the one used for the wild-type FokI and the four (or seven) codon insertion mutants that have been previously reported (12). The purity of the proteins were analyzed by 0.1% SDS-12% acrylamide gel electrophoresis (17), followed by staining the protein with coomassie blue (FIG. 2).

Preparation of DNA substrates with a single FokI site

Substrate containing a single *Fok*I site was constructed by forming a duplex using synthetic oligonucleotides SEQ ID NO:10 and SEQ ID NO:11 as shown in FIG. 3. The oligomers were phosphorylated and then annealed to form the duplex. The duplex is flanked by *Xba*I and *Hin*dIII compatible ends. The fragment was ligated to *Xba*I/*Hin*dIII-cleaved pTZ19R plasmid. The recombinants were screened for the insert using *Xba*I/*Hin*dIII digestion.

A 300-bp fragment containing the insert was gel-purified after digesting the recombinant plasmid with *Puv*II enzyme. The fragment was dephosphorylated by treatment with calf intestinal phosphatase (CIP) and then was rephosphorylated using T4 polynucleotide kinase and [$\beta^{32}$-P] ATP to obtain substrate that was labelled on both strands of the DNA. Digestion of the above labelled fragment with either *Hin*PI or *Xba*I, followed by gel-purification of the appropriate DNA fragment, yielded substrates that were labelled individually on each strand.

Figure 4:
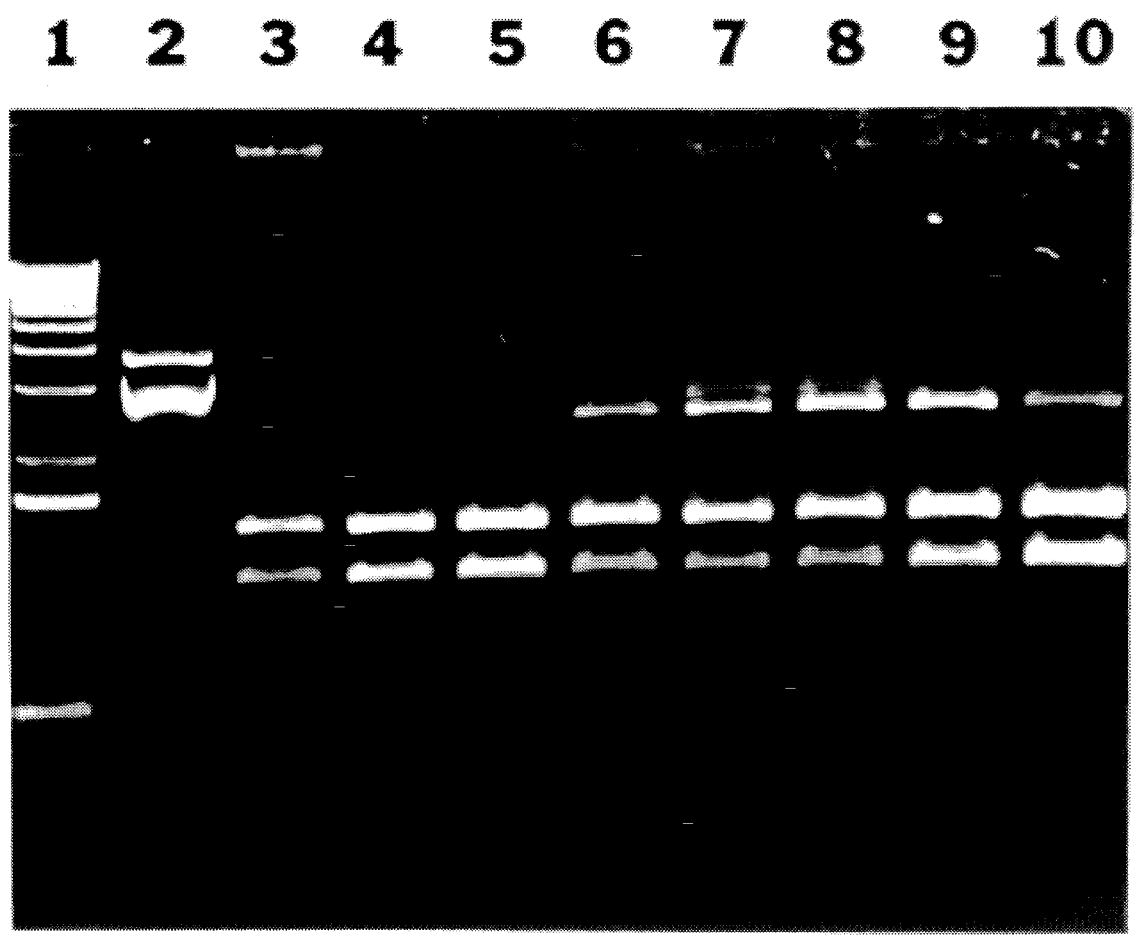
FIG. 4 shows the agarose gel electrophoretic profile of pTZ19R substrate cleavage by deletion and insertion mutants of FokI endonuclease. Lane 1, 1 kb ladder; lane 2, no enzyme; lane 3, KSEL (SEQ ID NO:3) deletion; lane 4, wild-type FokI; lane 5, TAEL (SEQ ID NO:4) insertion; lane 6, TAELTAEL (SEQ ID NO:5) insertion; lane 7, TAEL-TAELTAEL (SEQ ID NO:6) insertion; lane 8, 19 amino acid residue insertion, (SEQ ID NO:7); lane 9, 23 amino acid residue insertion, (SEQ ID NO:8) ; and lane 10, glycine linker insertion, (SEQ ID NO:9).
Figure 5:
FIG. 5 shows the PAGE (denaturing gel) profile of the digestion products of the DNA substrate containing a single FokI site by the deletion and insertion mutants of FokI endonuclease and corresponds to the 5'-GGATG--3' strand. Lanes G+A, Maxam-Gilbert (G+A) sequencing reactions using the substrate; lane 1, no enzyme; lane 2, KSEL (SEQ ID NO:3) deletion; lane 3, wild-type FokI; lane 4, TAEL (SEQ ID NO:4) insertion; lane 5, TAELTAEL (SEQ ID NO:5) insertion; lane 6, TAELTAELTAEL (SEQ ID NO:6) insertion; lane 7, 19 amino acid residue insertion, (SEQ ID NO:7); lane 8, 23 amino acid residue insertion, (SEQ ID NO:8); and lane 9, glycine linker insertion, (SEQ ID NO:9).
Figure 6:
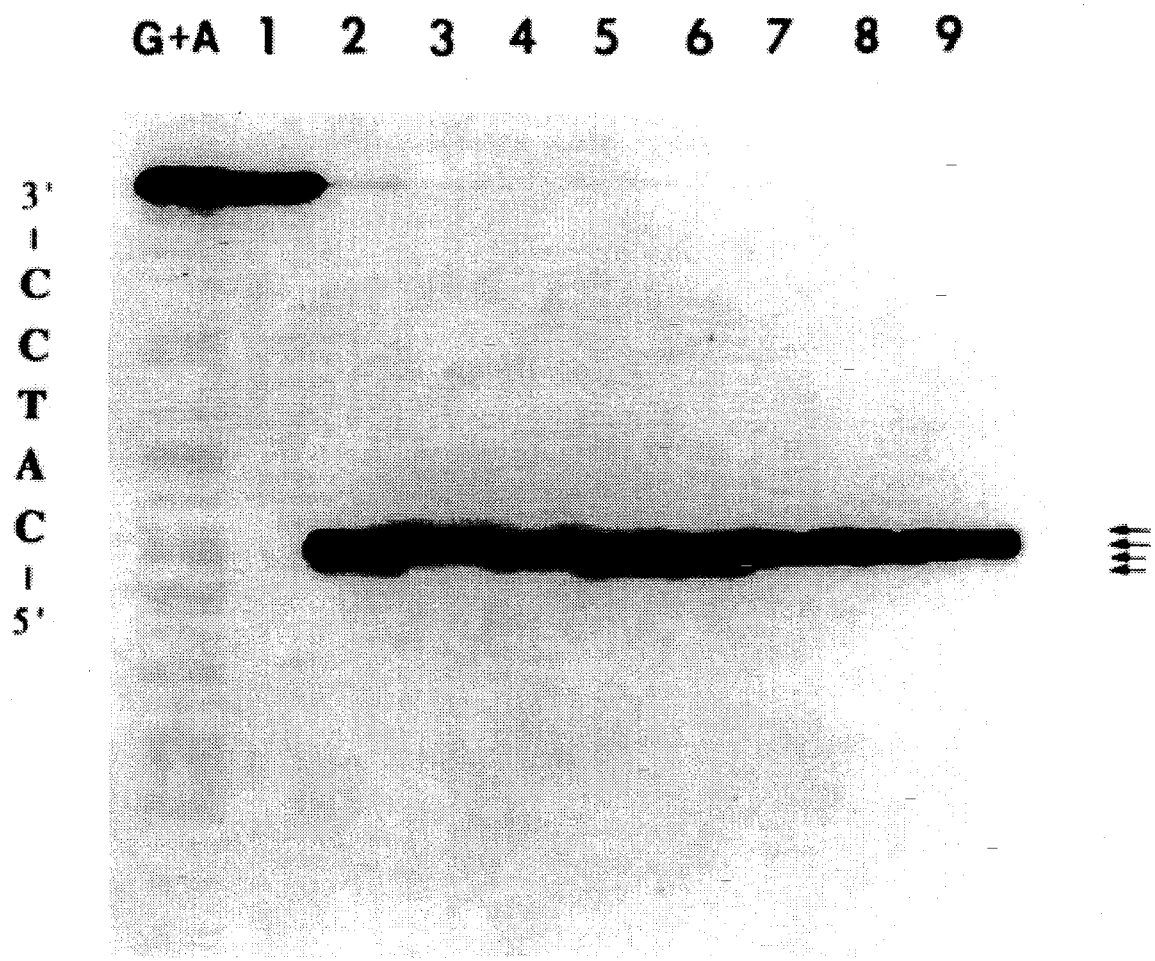
FIG. 6 shows the PAGE (denaturing gel) profile of the digestion products of the DNA substrate containing a single FokI site by the deletion and insertion mutants of FokI endonuclease and corresponds to the 5'-CATCC--3' strand. Lanes G+A, Maxam-Gilbert (G+A) sequencing reactions using the substrate; lane 1, no enzyme; lane 2, KSEL (SEQ ID NO:3) deletion; lane 3, wild-type FokI; lane 4, TAEL (SEQ ID NO:4) insertion; lane 5, TAELTAEL (SEQ ID NO:5) insertion; lane 6, TAELTAELTAEL (SEQ ID NO:6) insertion; lane 7, 19 amino acid residue insertion, (SEQ ID NO:7); lane 8, 23 amino acid residue insertion, (SEQ ID NO:8): and lane 9, glycine linker insertion, (SEQ ID NO:9).
Figure 7A:
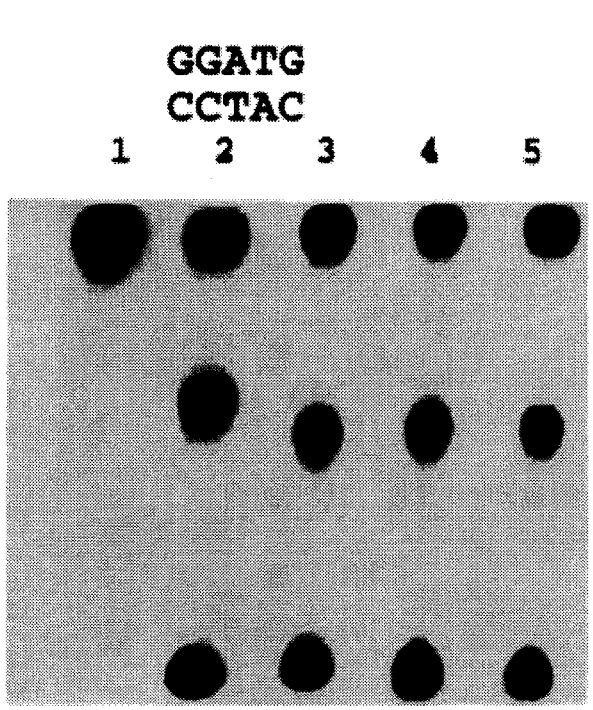
FIGS. 7A, 7B, 7C and 7D show the cleavage of unmethylated, hemi-methylated and fully methylated DNA substrates by wild-type FokI and the four codon, KSEL (SEQ ID NO:3) and TAEL (SEQ ID NO:4), insertion mutants.
Figure 7B:
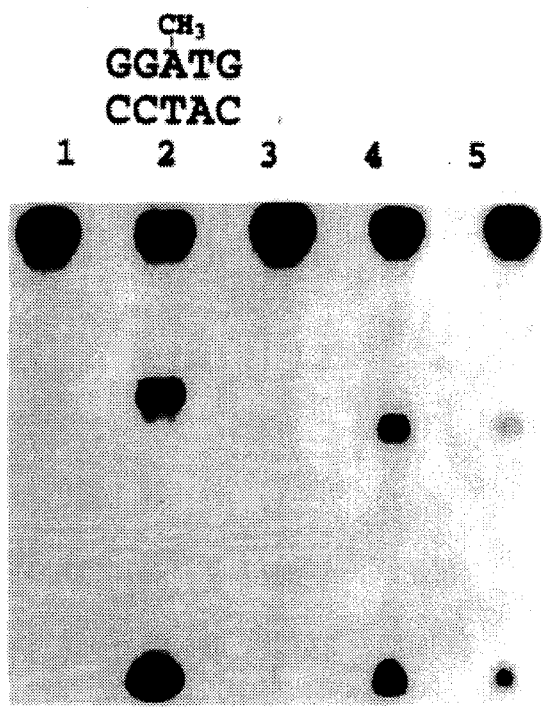
Figure 7C:
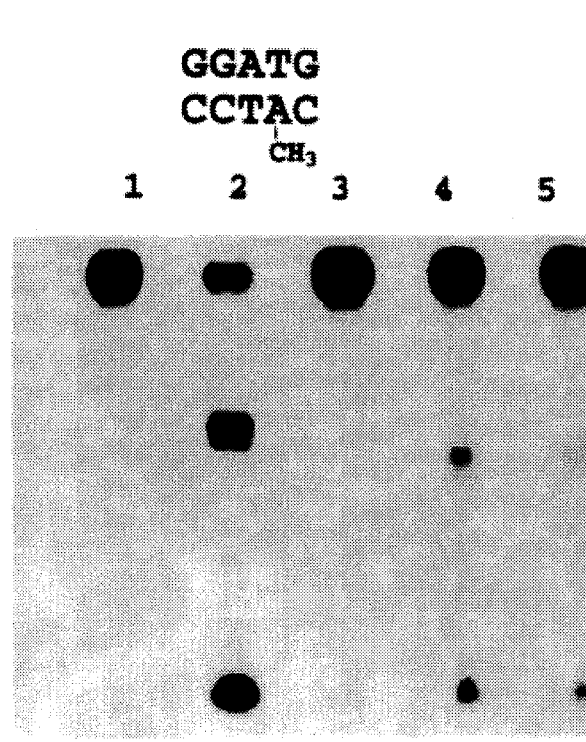
Figure 7D:
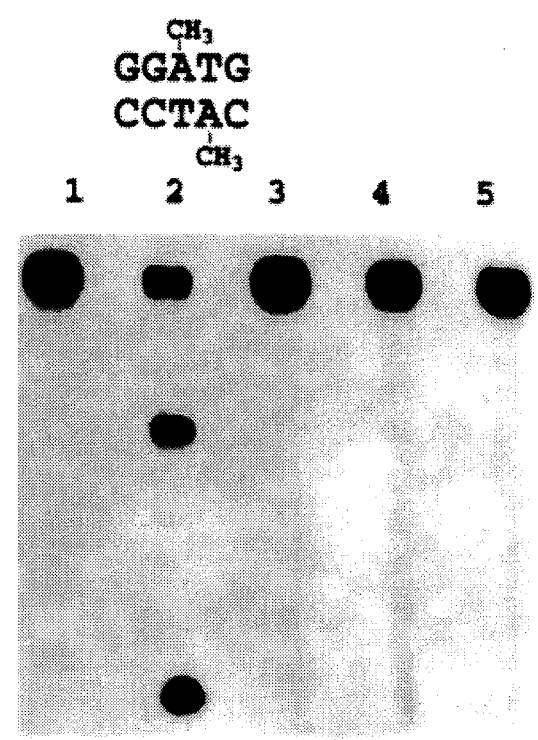

The cleavage assays with plasmid substrates were performed by adding pTZ19R (1.5μg) and the enzyme (40 nM) in a total reaction volume of 15 μl containing 10 mM Tris.HCl (pH 7.5 at 37° C.), 50 mM NaCl and 10 mM MgCl$_2$ and 1 mM DTE. The reactions were incubated at 37° C. for 4 hrs. The digests were analyzed by agarose gel (1.2%) electrophoresis (FIG. 4). For determining the cleavage distance from the recognition site within the DNA substrate, $^{32}$P-labelled substrates ($\cong$10,000 cpm) were mixed with 0.5 μg of pTZ19R and 45 nM of enzymes in a total volume of 10 μl containing 10 mM Tris. HCl (pH 7.5 at 37° C.), 50 mM NaCl, 10 mM MgCl$_2$ and 1 mM DTE. The reaction mixture was incubated at 37° C. for 2 hrs. The samples were subjected to electrophoresis on 7% PAGE containing 7M urea in 1 x TBE, the gel dried, and then exposed to x-ray film (FIGS. 5 and 6).

Cleavage of Hemi-Methylated DNA Substrates

The four oligonucleotides (SEQ ID NO:12, SEQ ID NO:13, hemi-methylated oligonucleotide of SEQ ID NO:12 and hemi-methylated oligonucleotide of SEQ ID NO:13) used in these experiments are the same oligonucleotides that were used by Waugh and Sauer to show that two of their eight *Fok*I endonuclease missense mutants cleave hemi-methylated DNA substrates (14). Each of the four oligomers were phosphorylated using T4 polynucleotide kinase and [$\beta^{32}$-P] ATP. By annealing various combinations of the synthetic substrates, it was possible to construct an unmethylated substrate, two hemi-methylated substrates and a fully methylated substrate. 0.02 picomole of each labelled substrate and about 70 nM sites (pTZ19R) were mixed with 70 nM of *Fok*I or insertion mutants, KSEL (SEQ ID NO:3) or TAEL (SEQ ID NO:4), in 15 μl of reaction buffer described above. The samples were analyzed on 9% PAGE containing 7 M urea, the gel was dried and then exposed to an x-ray film (FIG. 7).

Filter Binding Assays

The filter binding assays were performed in duplicate using *Fok*I or mutant enzymes and the four different synthetic substrates, SEQ ID NO:12, SEQ ID NO:13, hemi-methylated oligonucleotide of SEQ ID NO:12 and hemi-methylated oligonucleotide of SEQ ID NO:13. Nine different concentrations for each of the enzymes were made by serial dilutions (5000, 2000, 667, 222, 74.1, 24.7, 8.23, 2.74 and 0.914 nM). The enzymes were mixed with 40 nM of each labelled substrate along with 50 μg/ml p(dI-dC) and 50 μg/ml BSA in 50 μl of buffer A[10 mM Tris. phosphate (pH 8.0), 7 mM 2-mercaptoethanol, 1 mM EDTA, 50 mM NaCl, and 10% (vol/vol) glycerol]. The samples were incubated at 22° C. for 1 hr and then loaded on to nitrocellulose filters. The filters were washed twice with 0.5 ml of buffer A, dried and counted using the scintillation counter.

Construction of Insertion and Deletion Mutants of FokI Endonuclease

Previously, the present inventor has shown that introduction of additional amino acid residues (four or seven residues) between the recognition and cleavage domains of *Fok*I can alter the spacing between the recognition site and the cleavage site within the DNA substrate (12). Secondary structure prediction of *Fok*I endonuclease based on its primary amino acid sequence revealed a long stretch of α-helix region at the junction of the recognition and cleavage domains. If the helix constituted the linker that connects the two domains of the enzyme, the cleavage distance of *Fok*I from the recognition site could be altered by changing the length of this spacer. Insertion of either four codons or seven codons into the linker region of *Fok*I was expected to shift the cleavage distance one bp and two bp respectively away from the recognition site. Close examination of the amino acid sequence of the linker region revealed the presence of two KSEL (SEQ ID NO:3) repeats separated by amino acids EEK. Therefore, KSEL (SEQ ID NO:3) and KSELEEK (SEQ ID NO:14) were inserted within the linker region of *Fok*I. Both mutants cleaved DNA in a similar way and not necessarily in a distance-dependent way (12). Thus, a clear relationship between the length of the connector region of *Fok*I and the cleavage distance from the recognition site within its DNA substrate could not be established.

A direct relationship has been shown between the length of the protein connector regions of *Eco*R124 and *Eco*R124/3 (belonging to the Type I class) and their related but different recognition site 5'-GAA(N$_6$)RTGG--3' (SEQ ID NO:16) and 5'-GAA(N$_7$)RTGG-3' (SEQ ID NO:17), respectively, where R=G or A and N=G, A, T, or C. The recognition sites differ only in the length of the non-specific spacer. This difference nevertheless places the two specific domains of the *Eco*R124/3 sequence 3.4 Å further apart and rotates them 36° with respect to those of *Eco*R124, which implies major structural differences in the proteins recognizing the sequences (18). This is accommodated in the protein structure by altering the number of amino acid repeats (TAEL)$_2$ (SEQ ID NO:5) and (TAEL)$_3$ (SEQ ID NO:6), respectively, within the connector region (18).

To further probe the structure of the linker region between the recognition and cleavage domains of *Fok*I endonuclease, a series of mutants with various number of amino acid residue deletions or insertions ranging from −7 to +23 residues was constructed (Table I). The amino acid segments KSEL (SEQ ID NO:3), TAEL (SEQ ID NO:4) and KSELEEK (SEQ ID NO:14) were used as basic units of insertion or deletion. As indicated above, the TAEL (SEQ ID NO:4) segment was observed in the protein connector regions of *Eco*R124 and *Eco*R124/3 (Type I) enzymes. Multiples of the basic units and a combination thereof were inserted between the recognition and catalytic domains of *Fok*I to form the mutants. The method used to construct the insertion and deletion mutants are the same as the one previously reported (12). In addition, an 18 amino acid residue insertion mutant that includes the glycine linker, (Gly$_4$Ser)$_3$ (SEQ ID NO:15) was constructed. The clones of each mutant were induced with 1 mM IPTG for 4–5 hrs for optimal expression of the enzymes. The mutant enzymes were purified using the procedure previously described (10, 12). SDS/PAGE profiles of the mutant enzymes are shown in FIG. 2.

TABLE I

Insertion/deletion mutants of FokI restriction endonuclease

| aa sequence at the insertion/deletion site[1] | Number of aa insertion | Activity[2] |
|---|---|---|
| ... QLVKSELRHKLK ... | SEQ ID NO: 18 −7 | − |
| ... QLVEEKKSELRHKLK ... | SEQ ID NO: 19 −4 | + |
| ... QLVKSELEEKKSELRHKLK ... | SEQ ID NO: 20 wt | + |
| ... QLVTAELKSELEEKKSELRHKLK ... | SEQ ID NO: 21 +4 | + |
| ... QLVTAELTAELKSELEEKKSELRHKLK ... | SEQ ID NO: 22 +8 | + |
| ... QLVTAELTAELTAELKSELEEKKSELRHKLK ... | SEQ ID NO: 23 +12 | + |
| ... QLVTAELTAELKSELKSELEEKKSELEEKKSELRHKLK ... | SEQ ID NO: 24 +19 | + |
| ... QLVTAELTAELTAELKSELKSELEEKKSELEEKKSELRHKLK ... | SEQ ID NO: 25 +23 | + |
| ... QLRGGGGSGGGGSGGGGSQLVKSELEEKKSELRHKLK ... | SEQ ID NO: 26 +18[3] | + |

[1]The inserted aa residues are shown in bold-type.
[2]Activity based on the cleavage of pTZ19R DNA substrate. The cleavage pattern of the substrate by these mutants (as determined by the agarose gel electrophoresis) were similar to the wild-type (wt) FokI.
[3]The inserted aa residues contain (G—G—G—G—S)$_3$ linker. (SEQ ID NO:15)

Analysis of Sequence-Specificity and the Cleavage Distances from the Recognition Site of the Mutant Enzymes The agarose gel electrophoretic profile of the products of pTZ19R substrate cleavage by FokI and the deletion and insertion mutants are shown in FIG. 4. The profiles are very similar, suggesting that deletion and insertions ranging from −4 to +23 residues do not disrupt the sequence-specificity of the enzymes. Several clones of seven codon deletion mutants were identified; however, none of these clones showed any enzymatic activity indicating that seven residue (KSELEEK) (SEQ ID NO:14) deletion probably inactivates the enzyme. All digestions were done at similar protein concentrations. Larger insertion mutants show partial digests. These reactions proceed to completion either by increasing enzyme concentration or by digesting for longer time periods.

To determine the distance of cleavage by the insertion and deletion mutants from the recognition site, the cleavage products of the $^{32}$P-labeled DNA substrates containing a single FokI site were analyzed by PAGE (FIGS. 5 and 6). The digestion products were analyzed alongside the Maxam-Gilbert (G+A) sequencing reactions (19) of the substrates. The cut sites of the insertion mutants are all shifted one bp away from the recognition site on both strands of the DNA substrates as compared to the wild-type enzyme. A small amount of cleavage similar to that of wild-type enzyme is also observed. It is more pronounced with the four codon insertion (TAEL) (SEQ ID NO:4) mutant. Relaxation of specificity at the cut site is much more prevalent on the 5'-CATCC-3' strand than the 5'-GGATG-3 strand in the case of the insertion mutants. A similar relaxation of specificity at the cut site was observed with the "chimeric" restriction endonuclease produced by linking Ubx homeo domain to the cleavage domain of FokI (15). The four codon deletion (KSEL) (SEQ ID NO:3) mutant shows only relaxation of specificity at the cut site. The cleavage occurs predominantly at the site similar to the wild-type enzyme. The cut site is not shifted one bp closer to the recognition site as expected.

There appears to be no simple relationship between the length of the protein connector region of FokI and the cleavage distance from the recognition site within its DNA substrate. The recognition and cleavage domains of FokI are likely held together by a non-structured loop. There is probably some association between the recognition and nuclease domains of FokI. This domain—domain interaction is likely to be weak since mixing of the purified FokI recognition domain with the nuclease domain does not reconstitute FokI endonuclease. No sequence-specific cleavage of the substrate is observed with such a mixture; only non-specific nuclease activity is observed. Furthermore, the 18 amino acid residue insertion mutant that includes the glycine linker, (Gly$_4$Ser)$_3$ (SEQ ID NO:15), also shows the same sequence-specificity as the wild-type enzyme (FIG. 4, lane 10); it also cleaves predominantly one nucleotide further away from the recognition site on both strands of the DNA substrate (FIGS. 5 and 6; lane 9).

The glycine linker should neither exhibit a propensity for ordered secondary structure (20), nor show any tendency to interfere with the folding of the individual domains of the mutant enzyme. It is also unlikely to interfere with the domain-domain interaction that occurs due to the association of the two domains. This protein-protein interaction between the domains probably leads to the cleavage of the substrate at a precise distance from the recognition site by the mutant enzyme. This may also explain the absence of a linear relationship between the length of the linker region of FokI and cleavage distance from the recognition site within the DNA substrate.

The modular structure of FokI restriction endonuclease suggested that it may be feasible to engineer "chimeric" endonucleases with novel sequence-specificities by linking other DNA-binding domains to the cleavage domain of FokI endonuclease. Recently, the first chimeric restriction endonuclease has been successfully engineered by linking the Ubx homeo domain to the cleavage domain (F$_N$) of FokI (15).

In this regard, the present invention indicates that large insertions between the DNA-recognition domain and the catalytic domain of FokI do not disrupt the activity of the enzyme. Internal deletions of seven or more codons of the linker region appear to result in inactivation of the enzyme. These results are important for engineering "chimeric" restriction enzymes especially when one encounters protein-folding problems with the fusions.

In addition, "artificial" restriction enzymes with tailor-made sequence-specificities may be designed that would be used in the mapping and sequencing of large genomes. Thus, an array of artificial nucleases with designed specificities may be engineered for various applications.

More specifically, the mutants of the present invention have been designed for the same DNA sequence-specificity as the wild-type enzyme. However, the insertion mutants cleave predominantly one nucleotide further away from the recognition site on both strands of the DNA substrate. Thus, this invention provides new restriction enzymes with new cleavage sites compared to that of the wild type enzyme. Furthermore, the four codon deletion also provides a new restriction enzyme which exhibits relaxed specificity at the cut site while the seven codon deletion appears to inactivate the enzyme.

These engineered endonucleases will greatly facilitate the manipulation and mapping of genomic DNA and will be used to obtain information about protein structure and design.

Cleavage of Hemi-Methylated DNA Substrates by the Four Codon Insertion Mutants

Recently, Waugh and Sauer have identified a novel class of FokI restriction endonuclease mutants that cleave hemi-methylated substrates (14). To test if the deletion and insertion mutants of FokI cleave hemi-methylated DNA sites, the same four oligonucleotides described by Waugh and Sauer were used as substrates (SEQ ID NO:12, SEQ ID NO:13, hemi-methylated oligonucleotide of SEQ ID NO:12 and hemi-methylated oligonucleotide of SEQ ID NO:13). By annealing various combination of the $^{32}$P-labelled oligonucleotides, an unmethylated substrate, two hemi-methylated substrates and the fully methylated substrate were obtained. Cleavage assays with the hemi-methylated substrates were performed with the deletion and insertion mutants of FokI endonuclease. Of these, only the four codon insertion, TAEL (SEQ ID NO:4) and KSEL (SEQ ID NO:3), mutants cleave hemi-methylated substrates (FIG. 7A, 7B, 7C and 7D). Both the wild-type and the four codon insertion mutants cleave unmethylated substrate to yield two fragments, and none of the enzymes cleave the doubly methylated substrate. In addition, the two mutant enzymes and not the wild-type enzyme cleave both forms of hemi-methylated DNA. Although the cleavage of hemi-methylated substrates is not as efficient as the unmethylated substrate, it proceeds reasonably well. The TAEL (SEQ ID NO:4) insertion mutant appears to cleave the hemi-methylated substrates better than the KSEL (SEQ ID NO:3) insertion mutant.

Why does the four amino-acid residue insertions enable the mutant enzymes to cleave hemi-methylated DNA and not the larger inserts? The four codon insertions could increase the affinity of the mutants for the hemi-methylated DNA. The binding affinities of wild-type enzyme and both four codon insertion mutants were compared by filter binding assays using the synthetic oligonucleotide substrates (FIGS. 9A, 9B and 9C). The binding affinities were measured in the presence of non-specific DNA, poly dI-dC. The results suggest wild-type FokI can bind to hemi-methylated and even fully-methylated sites, although ~100 fold less efficiently than to unmethylated sites. The TAEL (SEQ ID NO:4) and KSEL (SEQ ID NO:3) insertion mutants show similar results suggesting that insertions do not affect the binding step. Furthermore, this model does not account for the inability of the larger insertion mutants to cleave hemi-methylated FokI sites.

In a more plausible model, the rate-limiting step of FokI cleavage reaction could involve the dissociation of the nuclease domain from the DNA-recognition domain. The methyl groups may inhibit the dissociation of the nuclease domain from the DNA-recognition domain through hydrophobic interactions or even stearic effects. The four amino acid residue insertions may have partly uncoupled the nuclease domain from the recognition domain resulting in the cleavage of the hemi-methylated substrates. Due to the added flexibility associated with large insertions, these may not uncouple the FokI nuclease domain from the DNA-binding domain. The model is consistent with the observation that "chimeric" restriction endonucleases obtained by linking other DNA-binding proteins to the nuclease domain of FokI exhibit not only sequence-specific cleavage that is determined by the DNA-binding protein but also non-specific nuclease activity which can be controlled by lowering the concentration of $MgCl_2$ (15). The dissociation of the enzyme from the cleaved product as a rate-limiting step in the FokI cleavage reaction could not be ruled out at this time.

In summary, the present results suggest that large insertions between the DNA-recognition domain and the catalytic domain of FokI do not disrupt the activity of the enzyme. Internal deletions of seven or more codons of the linker region appears to result in the inactivation of the enzyme. These findings are of importance for future engineering of "chimeric" restriction enzymes especially when one encounters protein-folding problems with the fusions. Several laboratories are in the process of determining the crystal structures of FokI and FokI-DNA complexes. These studies will provide detailed information about the mechanism of the FokI cleavage reaction and the domain-domain interactions within the protein-DNA complex at atomic resolution.

While the invention has been described in connection with what is presently considered to be the most practical and preferred embodiment, it is to be understood that the invention is not limited to the disclosed embodiment, but on the contrary is intended to cover various modifications and equivalent arrangements included within the spirit and scope of the appended claims.

Thus, it is to be understood that variations in the present invention can be made without departing from the novel aspects of this invention as defined in the claims.

The following scientific article have been cited throughout the present application and are hereby incorporated by reference in their entirety and relied upon:

(1) Sugisaki, H., and Kanazawa, S. (1992) Gene (Amst.) 6:73–78.

(2) Szybalski, W., Kim, S. C., Hanson, N., and Podhajska, A. J. (1991) Gene (Amst.) 100:13–26.

(3) Kita, K., Kotani, H., Sugisaki, H., and Takanami, M. (1989) J. Biol. Chem. 264:5751–5756.

(4) Looney, M. C., Moran, L. S., Jack, W. E., Feehery, G. R., Banner, J. S., Slatko, B. E., and Wilson G. G. (1994) Gene (Amst.) 80:193–208.

(5) Kita, K., Kotani, H., Hiraoko, N., Nakamura, T., and Yonaha, K. (1989) *Nucleic Acid Res.* 17:8741–8752.

(6) Kaczorowski, T., Skowron, P., and Podhajska. (1989) Gene (Amst.) 80:209–216.

(7) Skowron, P., Taczorowski, T., Tucholski, J., and Podhajska, A. J. (1993) Gene (Amst.) 125:1–10.

(8) Szybalski, W. (1985) Gene (Amst.) 40:169–173.

(9) Podhajska, A. J., and Szybalski, W. (1985) Gene (Amst.) 40:175–182.

(10) Li, L., Wu, L. P., and Chandrasegaran, S. (1992) *Proc. Natl. Acad. Sci. U.S.A.* 89:4275–4279.

(11) Li, L., Wu, L. P., Clarke, R., and Chandrasegaran, S. (1993) *Gene (Amst.)* 133:79–84.

(12) Li, L., and Chandrasegaran, S. (1993) *Proc. Natl. Acad. Sci. U.S.A.* 90:2764–2768.

(13) Waugh, D. S., and Sauer, R. T. (1993) *Proc. Natl. Acad. Sci. U.S.A.* 90:9596–9600.

(14) Waugh, D. S., and Sauer, R. T. (1994) *J. Biol. Chem.* 269:12298–12303.

(15) Kim, Y-G., and Chandrasegaran, S. (1994) *Proc. Natl. Acad. Sci. U.S.A.* 91:883–887.

(16) Sanger, F., Nicklen, S., and Coulson, A. R. (1977) *Proc. Natl. Acad. Sci. U.S.A.* 74:5463–5467.

(17) Laemmli, U.K. (1970) *Nature (London)* 222:680–685.

(18) Price, C., Lingner, J., Bickle, T. A., Firman, K., and Glover, S. W. (1989) J. Mol. Biol. 205:115–125.

(19) Maxam, A.M., and Gilbert, W. (1977) *Proc. Natl. Acad. Sci. U.S.A.* 74:560–564.

(20) Huston, J. S., Levinson, D., Mudgett-Hunter, M., Tai, M-S., Novotny, J., Margolies, M. N., Ridge, R. J., Bruccoleri, R. E., Haber, E., Crea, R., and Oppermann, H. (1988) *Proc. Natl. Acad. Sci. U.S.A.* 85:5879–5883.

What is claimed is:

1. A mutant *Fok*I endonuclease having an N-terminal DNA recognition domain and a C-terminal DNA cleavage domain, wherein said DNA recognition domain binds to a recognition site on a DNA substrate and said cleavage domain cuts at a cleavage site on said DNA substrate, wherein said recognition site is located at a distance from said cleavage site within said DNA substrate and wherein the distance between said recognition site and said cleavage site is shifted one base pair away from said recognition site as compared to said distance between said recognition site and said cleavage site recognized by wild-type enzyme.

2. A mutant *Fok*I endonuclease having an N-terminal DNA recognition domain and a C-terminal DNA cleavage domain, comprising an insertion between said recognition domain and said cleavage domain wherein said insertion is selected from the group consisting of SEQ ID NO:3, 4, 5, 6, 7, 8 and 9.

3. The endonuclease of claim 2, wherein said insertion consists of SEQ ID NO:3.

4. The endonuclease of claim 2, wherein said insertion consists of SEQ ID NO:4.

5. The endonuclease of claim 2, wherein said insertion consists of SEQ ID NO:5.

6. The endonuclease of claim 2, wherein said insertion consists of SEQ ID NO:6.

7. The endonuclease of claim 2, wherein said insertion consists of SEQ ID NO:7.

8. The endonuclease of claim 2, wherein said insertion consists of SEQ ID NO:8.

9. The endonuclease of claim 2, wherein said insertion consists of SEQ ID NO:9.

10. A mutant *Fok*I endonuclease having an N-terminal DNA recognition domain and a C-terminal DNA cleavage domain, comprising a deletion between said recognition domain and said cleavage domain wherein said deletion consists of SEQ ID NO:3.

* * * * *

SEQUENCE LISTING ( 1 ) GENERAL INFORMATION:

( i i i ) NUMBER OF SEQUENCES: 26

( 2 ) INFORMATION FOR SEQ ID NO:1:

( i ) SEQUENCE CHARACTERISTICS:
  ( A ) LENGTH: 40 base pairs
  ( B ) TYPE: nucleic acid
  ( C ) STRANDEDNESS: single
  ( D ) TOPOLOGY: linear ( i i ) MOLECULE TYPE: DNA ( x i ) SEQUENCE DESCRIPTION: SEQ ID NO:1:

GGCTCTAGAC GGCGGTGGAG GATCAGGGGG AGGAGGTAGC    40

( 2 ) INFORMATION FOR SEQ ID NO:2:

( i ) SEQUENCE CHARACTERISTICS:
  ( A ) LENGTH: 40 base pairs
  ( B ) TYPE: nucleic acid
  ( C ) STRANDEDNESS: single
  ( D ) TOPOLOGY: linear ( i i ) MOLECULE TYPE: DNA ( x i ) SEQUENCE DESCRIPTION: SEQ ID NO:2:

GGACTAGTTG TGATCCGCCT CCGCCGCTAC CTCCTCCCCC    40

( 2 ) INFORMATION FOR SEQ ID NO:3:

( i ) SEQUENCE CHARACTERISTICS:
  ( A ) LENGTH: 4 amino acids
  ( B ) TYPE: amino acid
  ( C ) STRANDEDNESS: single
  ( D ) TOPOLOGY: linear ( i i ) MOLECULE TYPE: PEPTIDE ( x i ) SEQUENCE DESCRIPTION: SEQ ID NO:3:

Lys Ser Glu Leu
1

( 2 ) INFORMATION FOR SEQ ID NO:4:

( i ) SEQUENCE CHARACTERISTICS:
  ( A ) LENGTH: 4 amino acids
  ( B ) TYPE: amino acid
  ( C ) STRANDEDNESS: single
  ( D ) TOPOLOGY: linear ( i i ) MOLECULE TYPE: PEPTIDE ( x i ) SEQUENCE DESCRIPTION: SEQ ID NO:4:

Thr Ala Glu Leu
1

( 2 ) INFORMATION FOR SEQ ID NO:5:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: PEPTIDE ( x i ) SEQUENCE DESCRIPTION: SEQ ID NO:5:

Thr Ala Glu Leu Thr Ala Glu Leu
1               5

( 2 ) INFORMATION FOR SEQ ID NO:6:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: PEPTIDE ( x i ) SEQUENCE DESCRIPTION: SEQ ID NO:6:

Thr Ala Glu Leu Thr Ala Glu Leu Thr Ala Glu Leu
1               5                   10

( 2 ) INFORMATION FOR SEQ ID NO:7:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: PEPTIDE ( x i ) SEQUENCE DESCRIPTION: SEQ ID NO:7:

Thr Ala Glu Leu Thr Ala Glu Leu Lys Ser Glu Leu Lys Ser Glu Leu
1               5                   10                  15

Glu Glu Lys ( 2 ) INFORMATION FOR SEQ ID NO:8:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( i i ) MOLECULE TYPE: PEPTIDE ( x i ) SEQUENCE DESCRIPTION: SEQ ID NO:8:

Thr Ala Glu Leu Thr Ala Glu Leu Thr Ala Glu Leu Lys Ser Glu Leu
1               5                   10                  15

Lys Ser Glu Leu Glu Glu Lys
                20

( 2 ) INFORMATION FOR SEQ ID NO:9:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( i i ) MOLECULE TYPE: PEPTIDE ( x i ) SEQUENCE DESCRIPTION: SEQ ID NO:9:

Arg Gly Gly Gly Gly Ser Gly Gly Gly Gly Ser Gly Gly Gly Gly Ser
1               5                   10                  15

Gln Leu ( 2 ) INFORMATION FOR SEQ ID NO:10:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:10:

CTAGAGTCAG ATAGCGAAGA CTTCGGGGAT GGGCTTAATG GCCTTAGTTC ACAA 54

( 2 ) INFORMATION FOR SEQ ID NO:11:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:11:

AGCTTTGTGA ACTAAGGCCA TTAAGCCCAT CCCCGAAGTC TTCGCTATCT GACT 54

( 2 ) INFORMATION FOR SEQ ID NO:12:

( i ) SEQUENCE CHARACTERISTICS:
        ( A ) LENGTH: 62 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:12:

CTAGAGTCAG AATTCGAAGA CTTGCCGGAT GATCTGCAGG CCAGCTGTGG CGTCTAAATT 60

GA 62

( 2 ) INFORMATION FOR SEQ ID NO:13:

( i ) SEQUENCE CHARACTERISTICS:
        ( A ) LENGTH: 62 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:13:

AGCTTCAATT TAGACGCCAC AGCTGGCCTG CAGATCATCC GGCAAGTCTT CGAATTCTGA 60

CT 62

( 2 ) INFORMATION FOR SEQ ID NO:14:

( i ) SEQUENCE CHARACTERISTICS:
        ( A ) LENGTH: 7 amino acids
        ( B ) TYPE: amino acid ( C ) STRANDEDNESS: single
            ( D ) TOPOLOGY: linear ( i i ) MOLECULE TYPE: PEPTIDE ( x i ) SEQUENCE DESCRIPTION: SEQ ID NO:14:

Lys  Ser  Glu  Leu  Glu  Glu  Lys
    1                 5

( 2 ) INFORMATION FOR SEQ ID NO:15:

( i ) SEQUENCE CHARACTERISTICS:
            ( A ) LENGTH: 15 amino acids
            ( B ) TYPE: amino acid
            ( C ) STRANDEDNESS: single
            ( D ) TOPOLOGY: linear ( i i ) MOLECULE TYPE: PEPTIDE ( x i ) SEQUENCE DESCRIPTION: SEQ ID NO:15:

Gly  Gly  Gly  Gly  Ser  Gly  Gly  Gly  Gly  Ser  Gly  Gly  Gly  Gly  Ser
    1                 5                           1 0                          1 5

( 2 ) INFORMATION FOR SEQ ID NO:16:

( i ) SEQUENCE CHARACTERISTICS:
            ( A ) LENGTH: 13 amino acids
            ( B ) TYPE: amino acid
            ( C ) STRANDEDNESS: single
            ( D ) TOPOLOGY: linear ( i i ) MOLECULE TYPE: PEPTIDE ( x i ) SEQUENCE DESCRIPTION: SEQ ID NO:16:

Gly  Ala  Ala  Asn  Asn  Asn  Asn  Asn  Asn  Arg  Thr  Gly  Gly
    1                 5                           1 0

( 2 ) INFORMATION FOR SEQ ID NO:17:

( i ) SEQUENCE CHARACTERISTICS:
            ( A ) LENGTH: 14 amino acids
            ( B ) TYPE: amino acid
            ( C ) STRANDEDNESS: single
            ( D ) TOPOLOGY: linear ( i i ) MOLECULE TYPE: PEPTIDE ( x i ) SEQUENCE DESCRIPTION: SEQ ID NO:17:

Gly  Ala  Ala  Asn  Asn  Asn  Asn  Asn  Asn  Asn  Arg  Thr  Gly  Gly
    1                 5                           1 0

( 2 ) INFORMATION FOR SEQ ID NO:18:

( i ) SEQUENCE CHARACTERISTICS:
            ( A ) LENGTH: 12 amino acids
            ( B ) TYPE: amino acid
            ( C ) STRANDEDNESS: single
            ( D ) TOPOLOGY: linear ( i i ) MOLECULE TYPE: PEPTIDE ( x i ) SEQUENCE DESCRIPTION: SEQ ID NO:18:

Gln  Leu  Val  Lys  Ser  Glu  Leu  Arg  His  Lys  Leu  Lys
    1                 5                           1 0

( 2 ) INFORMATION FOR SEQ ID NO:19:

( i ) SEQUENCE CHARACTERISTICS:
            ( A ) LENGTH: 15 amino acids
            ( B ) TYPE: amino acid (C) STRANDEDNESS: single
(D) TOPOLOGY: linear (ii) MOLECULE TYPE: PEPTIDE (xi) SEQUENCE DESCRIPTION: SEQ ID NO:19:

Gln Leu Val Glu Glu Lys Lys Ser Glu Leu Arg His Lys Leu Lys
1               5                   10                  15

(2) INFORMATION FOR SEQ ID NO:20:

(i) SEQUENCE CHARACTERISTICS:
    (A) LENGTH: 19 amino acids
    (B) TYPE: amino acid
    (C) STRANDEDNESS: single
    (D) TOPOLOGY: linear (ii) MOLECULE TYPE: PEPTIDE (xi) SEQUENCE DESCRIPTION: SEQ ID NO:20:

Gln Leu Val Lys Ser Glu Leu Glu Glu Lys Lys Ser Glu Leu Arg His
1               5                   10                  15

Lys Leu Lys (2) INFORMATION FOR SEQ ID NO:21:

(i) SEQUENCE CHARACTERISTICS:
    (A) LENGTH: 23 amino acids
    (B) TYPE: amino acid
    (C) STRANDEDNESS: single
    (D) TOPOLOGY: linear (ii) MOLECULE TYPE: PEPTIDE (xi) SEQUENCE DESCRIPTION: SEQ ID NO:21:

Gln Leu Val Thr Ala Glu Leu Lys Ser Glu Leu Glu Glu Lys Lys Ser
1               5                   10                  15

Glu Leu Arg His Lys Leu Lys
            20

(2) INFORMATION FOR SEQ ID NO:22:

(i) SEQUENCE CHARACTERISTICS:
    (A) LENGTH: 27 amino acids
    (B) TYPE: amino acid
    (C) STRANDEDNESS: single
    (D) TOPOLOGY: linear (ii) MOLECULE TYPE: PEPTIDE (xi) SEQUENCE DESCRIPTION: SEQ ID NO:22:

Gln Leu Val Thr Ala Glu Leu Thr Ala Glu Leu Lys Ser Glu Leu Glu
1               5                   10                  15

Glu Lys Lys Ser Glu Leu Arg His Lys Leu Lys
            20                  25

(2) INFORMATION FOR SEQ ID NO:23:

(i) SEQUENCE CHARACTERISTICS:
    (A) LENGTH: 31 amino acids
    (B) TYPE: amino acid
    (C) STRANDEDNESS: single
    (D) TOPOLOGY: linear (ii) MOLECULE TYPE: PEPTIDE (xi) SEQUENCE DESCRIPTION: SEQ ID NO:23:

Gln Leu Val Thr Ala Glu Leu Thr Ala Glu Leu Thr Ala Glu Leu Lys

```
           1              5                     10                      15
        Ser Glu Leu Glu Glu Lys Lys Ser Glu Leu Arg His Lys Leu Lys
                        20                    25                      30
```

(2) INFORMATION FOR SEQ ID NO:24:

(i) SEQUENCE CHARACTERISTICS:
        (A) LENGTH: 38 amino acids
        (B) TYPE: amino acid
        (C) STRANDEDNESS: single
        (D) TOPOLOGY: linear (ii) MOLECULE TYPE: PEPTIDE (xi) SEQUENCE DESCRIPTION: SEQ ID NO:24:

```
        Gln Leu Val Thr Ala Glu Leu Thr Ala Glu Leu Lys Ser Glu Leu Lys
        1              5                     10                      15

Ser Glu Leu Glu Glu Lys Lys Ser Glu Leu Glu Glu Lys Lys Ser Glu
                        20                    25                      30

Leu Arg His Lys Leu Lys
                        35
```

(2) INFORMATION FOR SEQ ID NO:25:

(i) SEQUENCE CHARACTERISTICS:
        (A) LENGTH: 42 amino acids
        (B) TYPE: amino acid
        (C) STRANDEDNESS: single
        (D) TOPOLOGY: linear (ii) MOLECULE TYPE: PEPTIDE (xi) SEQUENCE DESCRIPTION: SEQ ID NO:25:

```
        Gln Leu Val Thr Ala Glu Leu Thr Ala Glu Leu Thr Ala Glu Leu Lys
        1              5                     10                      15

Ser Glu Leu Lys Ser Glu Leu Glu Glu Lys Lys Ser Glu Leu Glu Glu
                        20                    25                      30

Lys Lys Ser Glu Leu Arg His Lys Leu Lys
                        35                    40
```

(2) INFORMATION FOR SEQ ID NO:26:

(i) SEQUENCE CHARACTERISTICS:
        (A) LENGTH: 37 amino acids
        (B) TYPE: amino acid
        (C) STRANDEDNESS: single
        (D) TOPOLOGY: linear (ii) MOLECULE TYPE: PEPTIDE (xi) SEQUENCE DESCRIPTION: SEQ ID NO:26:

```
        Gln Leu Arg Gly Gly Gly Gly Ser Gly Gly Gly Gly Ser Gly Gly Gly
        1              5                     10                      15

Gly Ser Gln Leu Val Lys Ser Glu Leu Glu Glu Lys Lys Ser Glu Leu
                        20                    25                      30

Arg His Lys Leu Lys
                        35
```